United States Patent [19]

Brinker et al.

[11] Patent Number: 5,589,649
[45] Date of Patent: Dec. 31, 1996

[54] DISSOLUTION TESTING APPARATUS

[75] Inventors: Gerald Brinker, North Brunswick; Peter Hladik, Piscataway, both of N.J.; Alan Gutwillig, Sterling, Va.

[73] Assignee: Distek, Inc., North Brunswick, N.J.

[21] Appl. No.: 389,063

[22] Filed: Feb. 14, 1995

Related U.S. Application Data

[63] Continuation of Ser. No. 201,633, Feb. 25, 1994, abandoned.

[51] Int. Cl.⁶ .............................. G01N 13/00; B01L 7/00
[52] U.S. Cl. ..................... 73/866; 422/68.1; 366/143; 366/343; 219/385
[58] Field of Search .............................. 73/53.01, 54.35, 73/54.38, 54.43, 866, 54.31; 422/68.1; 366/142, 143, 144, 197, 198, 249, 343; 219/385, 435, 521

[56] References Cited

U.S. PATENT DOCUMENTS

| | | | |
|---|---|---|---|
| 3,092,704 | 6/1963 | De Woody et al. | 219/385 |
| 3,109,913 | 11/1963 | Galajda | 366/146 |
| 3,665,761 | 5/1972 | Gregory | 374/31 |
| 3,765,655 | 10/1973 | Lutinen | 366/326 |
| 3,791,221 | 2/1974 | Kirschner et al. | 73/866 |
| 3,791,222 | 2/1974 | Goodhart et al. | 73/866 |
| 3,802,272 | 4/1974 | Bischoff et al. | 73/866 |
| 3,877,817 | 4/1975 | Ralston | 356/409 |
| 3,935,726 | 2/1976 | Heinz | 73/54.35 |
| 4,279,860 | 6/1981 | Smolen | 422/63 |
| 4,335,438 | 6/1982 | Smolen | 364/497 |
| 4,464,340 | 8/1984 | Lennox, Jr. et al. | 422/103 |
| 4,466,276 | 8/1984 | Ruyak et al. | 73/54.35 |
| 4,681,858 | 7/1987 | Chaudhari et al. | 436/165 |
| 4,704,035 | 11/1987 | Kowalczyk | 366/142 |
| 4,715,723 | 12/1987 | Anderson et al. | 366/142 |
| 4,754,657 | 7/1988 | Schneider | 73/866 |
| 4,856,909 | 8/1989 | Mehta et al. | 73/866 |
| 4,858,155 | 8/1989 | Okawa et al. | 364/557 |
| 4,879,917 | 11/1989 | Eppelmann et al. | 73/866 |
| 4,924,716 | 5/1990 | Schneider | 73/866 |
| 5,011,662 | 4/1991 | Noormohammadi et al. | 422/68.1 |
| 5,023,187 | 6/1991 | Koebler et al. | 436/180 |
| 5,080,232 | 1/1992 | Leoncavallo et al. | 206/446 |
| 5,280,678 | 1/1994 | Jennings | 34/30 |

FOREIGN PATENT DOCUMENTS

| | | |
|---|---|---|
| 0278374 | 8/1988 | European Pat. Off. . |
| 0757616 | 9/1956 | United Kingdom . |
| 9210294 | 6/1992 | WIPO . |

OTHER PUBLICATIONS

United States Pharmacopeia (USP), Chapter XXII, Section 711, Dissolution, dated 1990.

*Primary Examiner*—Hezron E. Williams
*Assistant Examiner*—Michael J. Brock
*Attorney, Agent, or Firm*—Steve Mendelsohn; William H. Murray

[57] ABSTRACT

The dissolution testing apparatus has a plurality of stirring elements for stirring the test solutions within a plurality of test vessels with reflective surfaces. The temperatures of the test solutions are individually controlled by a temperature control system. The temperature control system includes a controller, a heating element for each test vessel to heat the corresponding test solution, and a temperature sensor for each test vessel to measure the temperature of the corresponding test solution. The heating elements are wrapped around the outside of the test vessels and held in place by spring-loaded heater jackets. Each stirring element has a hollow shaft, a detachable stirring attachment (e.g., blade or basket), a temperature sensor inside the hollow shaft, and a signal transfer device to transmit signals from the temperature sensor to the controller. The test vessels are supported and aligned with respect to the stirring elements with a holding plate having openings and corresponding alignment fixtures.

63 Claims, 13 Drawing Sheets

FIG. 10. PADDLE-TYPE DISSOLUTION TEST PROCEDURE

FIG. 11. BASKET-TYPE DISSOLUTION TEST PROCEDURE

DISSOLUTION TESTING APPARATUS

This is a continuation of application Ser. No. 08/201,633 filed on Feb. 25, 1994 now abandoned.

BACKGROUND OF THE INVENTION

1. Field of the Invention

The present invention relates to the field of dissolution testing and, in particular, to apparatuses for dissolution testing of pharmaceuticals in solid, semi-solid, or transdermal dosage form.

2. Description of the Related Art

Dissolution testing and apparatuses for performing such are known in the art. U.S. Pat. No. 4,279,860 (Smolen) and U.S. Pat. No. 4,335,438 (Smolen) provide descriptions of the art of dissolution testing. In general, dissolution testing is used to determine the rate of dissolution of a material in a solution. For example, dissolution testing may be used to determine the rate of dissolution of pharmaceuticals in dosage form in specific test solutions to simulate digestion in a human. The requirements for such dissolution testing apparatuses are provided in United States Pharmacopeia (USP), Edition XXII, Section 711, Dissolution (1990).

Conventional dissolution testing apparatuses have one or more test vessels in which test solutions may be placed. One conventional configuration of a dissolution testing apparatus has, for each test vessel, a basket-type stirring element consisting of a metal shaft with a cylindrical basket at the end. After placing the dosage to be dissolved into the basket, the stirring element is lowered into the test solution near the center of the vessel and rotated at a specified rate (typically measured in revolutions per minute (RPM)) for a specified duration. Samples of the test solutions may be periodically withdrawn from the vessels to determine the degree of dissolution of the dosages as a function of time.

Another conventional configuration of a dissolution testing apparatus has a paddle-type stirring element consisting of a metal shaft with a metal blade at the end. In dissolution testing with this type of apparatus, the stirring element is rotated within the test solution with the dosage at the bottom of the vessel.

In either conventional configuration, the temperature of the test solutions is maintained at the required level (e.g., 37 degrees centigrade) by placing the test vessels in a water bath. The temperature of the water bath is typically controlled by an external water pump/heater which continually recycles water between the water bath and the pump/heater. The temperature of a test solution within one of the test vessels may be measured directly by inserting a thermometer into the test solution or indirectly by measuring the temperature of the water bath, either in the water bath itself or within the water pump/heater. Direct temperature measurement of the test solutions is not permitted during the actual dissolution testing procedure. As a result, only indirect temperature measurements are available during the testing procedure.

Conventional dissolution testing apparatuses have a number of problems. As just discussed, conventional apparatuses do not support direct measurement of test solution temperatures during testing procedures. Moreover, since all test vessels of a dissolution testing apparatus are placed within the same water bath, the temperatures for all test solutions for a specific testing procedure are the same. In addition, water baths have problems related to leaking, evaporation, and algae growth. As a result, water baths must be emptied, cleaned, and refilled periodically. Furthermore, the time required to heat test solutions using conventional water bath dissolution testing apparatuses is long—typically 30 to 45 minutes.

What is needed is an improved dissolution testing apparatus that eliminates or reduces the problems associated with conventional apparatuses.

It is accordingly an object of this invention to overcome the disadvantages and drawbacks of the known art and to provide improved apparatuses for dissolution testing.

It is a further object of this invention to provide a dissolution testing apparatus that does not rely upon a water bath to control the temperature of the test solutions in one or more test vessels.

It is another object of this invention to provide a dissolution testing apparatus that provides for direct measurement of test solution temperature during actual dissolution testing procedures and still conform to the USP dissolution test requirements.

It is yet another object of this invention to provide a dissolution testing apparatus that reduces the time required to heat the test solutions to the desired levels for dissolution testing.

Further objects and advantages of this invention will become apparent from the detailed description of a preferred embodiment which follows.

SUMMARY OF THE INVENTION

The present invention is an apparatus for dissolution testing of a material in a test solution within a test vessel. According to a preferred embodiment, the apparatus comprises (a) a stirring element for stirring the test solution; (b) a heating element placed around the outside of the test vessel for heating the test solution; and (c) a controller for controlling the heating element to control the temperature of the test solution.

According to an alternative preferred embodiment of the present invention, the apparatus comprises a stirring element for stirring the test solution. The stirring element comprises (1) a hollow stirring assembly; and (2) a temperature sensor located within the hollow stirring assembly for generating signals representative of the temperature of the test solution.

According to another alternative preferred embodiment of the present invention, the apparatus comprises (a) a test vessel for holding the test solution and the material, wherein the test vessel comprises a reflective surface; and (b) a stirring element for stirring the test solution.

According to yet another alternative preferred embodiment of the present invention, the apparatus comprises a stirring element for stirring the test solution. The stirring element comprises (1) a shaft and (2) a stirring element attachment, adapted to be removably coupled to the shaft.

According to still another alternative preferred embodiment of the present invention, the apparatus comprises (a) a stirring element for stirring the test solution; and (b) a holding plate having at least one opening for receiving and supporting the test vessel. The holding plate comprises a plurality of alignment fixtures for aligning the test vessel with respect to the stirring element.

The present invention is also an apparatus for dissolution testing of a plurality of materials in a plurality of test solutions within a plurality of test vessels. For each test vessel, the apparatus preferably comprises a stirring element for stirring the test solution; a heating element placed around the outside of the test vessel for heating the test solution; a heater jacket surrounding the heating element for holding the heating element in place around the test vessel; and a controller. Each stirring element comprises (1) a hollow shaft; (2) a stirring element attachment, adapted to be removably coupled to the hollow shaft, wherein the stirring element attachment is one of a blade attachment and a basket attachment; (3) a temperature sensor located within the hollow shaft for generating signals representative of the temperature of the test solution when the hollow shaft is inserted into the test solution; and (4) a signal transfer device for transmitting the signals from the temperature sensor while the stirring element stirs the test solution. The controller controls each heating element to control the temperature of each test solution in accordance with the signals from each temperature sensor. The heater jacket and heating element are configured to permit viewing of the stirring element through the front of the test vessel when the stirring element is inserted into the test vessel. The heater jacket and the heating element are also configured to provide a gap between the outer surface of the heating element and the inner surface of the heater jacket. The heating element has two heating areas with different power ratings.

The present invention is also a test vessel for use with an apparatus for dissolution testing of a material in a test solution, wherein the test vessel comprises a reflective surface.

BRIEF DESCRIPTION OF THE DRAWINGS

Other objects, features, and advantages of the present invention will become more fully apparent from the following detailed description of the preferred embodiment, the appended claims, and the accompanying drawings in which:

DESCRIPTION OF THE PREFERRED EMBODIMENT(S)

The present invention is directed to a dissolution testing apparatus having a plurality of test vessels and a plurality of stirring elements. The temperatures of the solutions placed in the test vessels for dissolution testing are individually controlled by a temperature control system. The temperature control system includes a controller, a heating element for each test vessel to heat the test solution, and a temperature sensor for each test vessel to measure the temperature of the test solution. In a preferred embodiment, the heating elements are wrapped around the outside of the test vessels and the temperature sensors are placed within the hollow shafts of the stirring elements. In addition, the test vessels preferably have a reflective surface and the stirring elements have interchangeable attachments such as blade and basket attachments.

Figure 1:
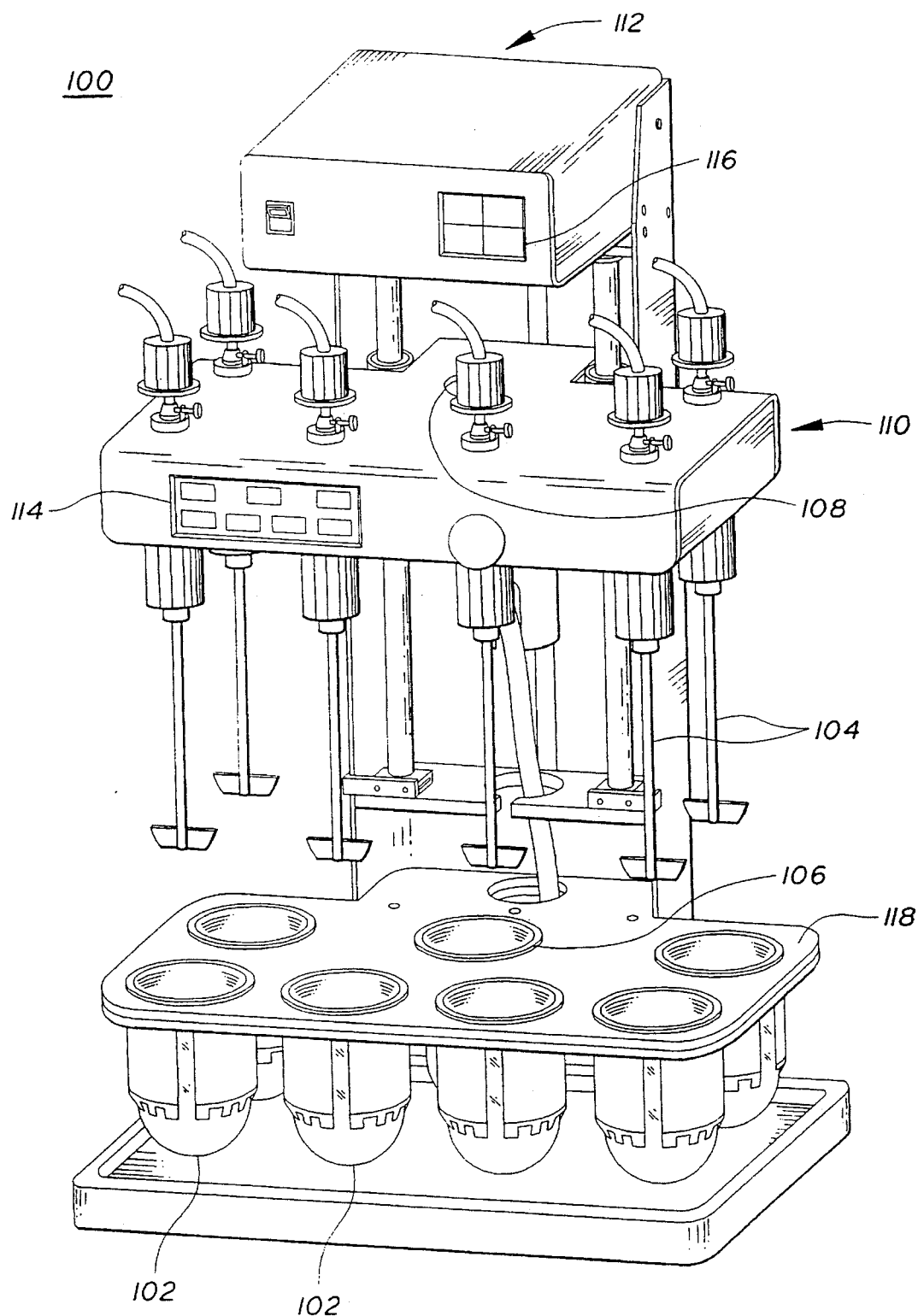
FIG. 1 shows a perspective view of a dissolution testing apparatus, according to a preferred embodiment of the present invention.

Referring now to FIG. 1, there is shown a dissolution testing apparatus 100, according to a preferred embodiment of the present invention. Dissolution testing apparatus 100 has six test vessels 102 and six corresponding stirring elements 104. A seventh test vessel 106 may be used as an unstirred control vessel during dissolution testing. Apparatus 100 has a port 108 that may optionally be used to configure apparatus 100 with a seventh stirring element corresponding to the seventh test vessel 106. The test vessels 102, 106 are held in place within test vessel holding plate 118. As shown in FIG. 1, the stirring elements 104 are configured as paddle-type stirring elements.

Dissolution testing apparatus 100 also has a drive system 110 to lower the stirring elements 104 into the test vessels 102 at the start of dissolution testing, to rotate the stirring elements 104 about their shaft axes during dissolution testing, and to raise the stirring elements 104 out of the test vessels 102 at the end of dissolution testing. Such drive systems are known in the art of dissolution testing.

The operations of apparatus 100 are controlled by controller 112. LCD display 114 preferably has seven fields, one for each test vessel 102, that may be used to display the current temperature of the test vessel or the current power in watts being used to heat the test vessel. LED display 116 preferably has four fields that may be used to display simultaneously the information related to the following: (1) average test vessel temperature; (2) current stirring element rate (in RPM); (3) elapsed time of dissolution test; and (4) time of next solution sampling.

Figure 2:
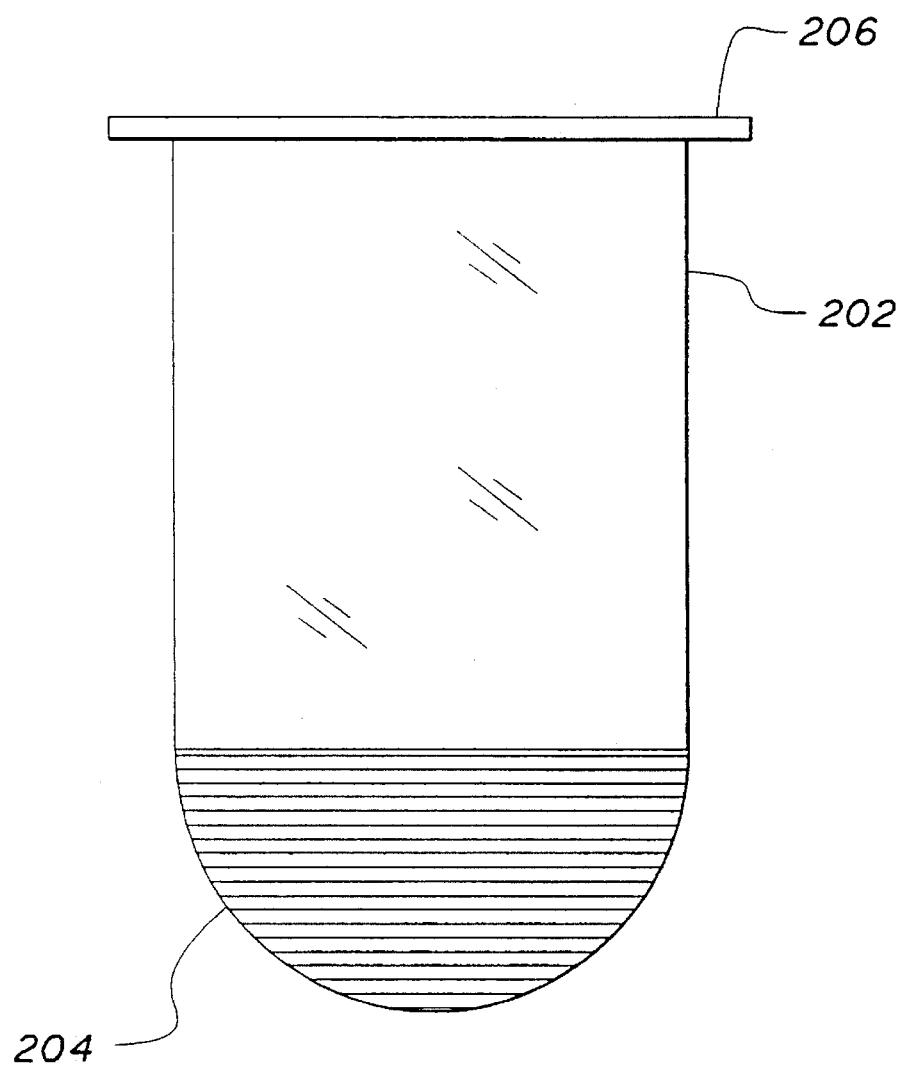
FIG. 2 is a front view of a test vessel of the apparatus of FIG. 1.

Referring now to FIG. 2, there is shown a front view of a test vessel 102, according to a preferred embodiment of the present invention. Test vessel 102 may vary in size from 50-milliliter capacity to 4-liter capacity. The preferred size may be dictated by the appropriate UPS regulations.

Test vessel 102 has a cylindrical portion 202, a semi-spherical portion 204, and a flange 206. The outer diameter (OD) of the flange 206 is preferably greater than the OD of the cylindrical portion 202. The semi-spherical portion 204 preferably has a reflective coating, such as but not limited to a mirrored coating, to provide test vessel 102 with a reflective surface that inhibits the flow of heat out of the test vessel 102. Those skilled in the art will understand that the purpose of such a reflective surface is to improve warm-up characteristics and temperature control of the test solution by reducing heat loss from the test vessel and reducing the time required to bring the test solution to the desired temperature.

Figure 3:
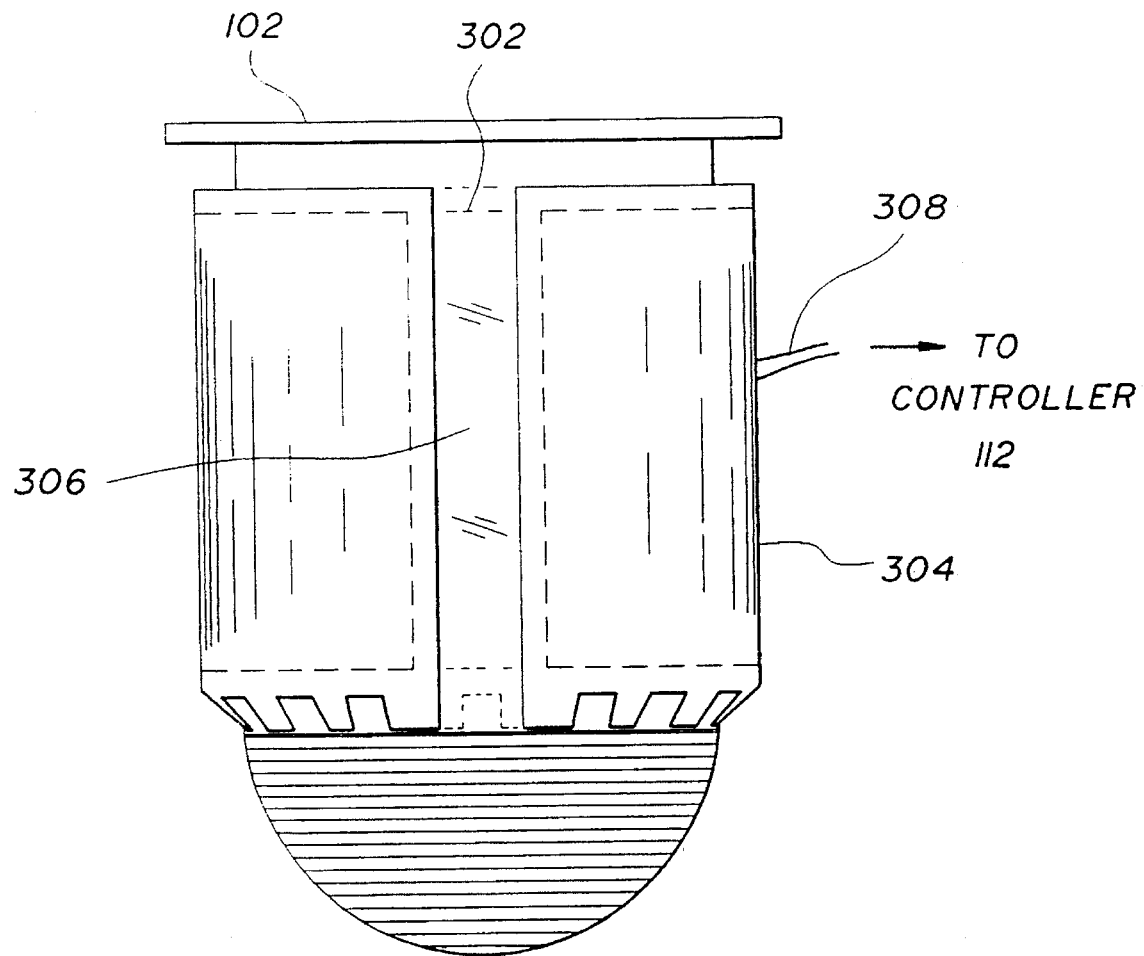
FIG. 3 shows a front view of a test vessel of the apparatus of FIG. 1, configured with a heater assembly.

Referring now to FIG. 3, there is shown a front view of a test vessel 102 of apparatus 100 of FIG. 1, configured with a heater assembly. According to the present invention, test vessel 102 is wrapped with a heating element 302 that is held in place by a spring-loaded stainless steel heater jacket 304. The configuration of heating element 302 and heater jacket 304 preferably provides a port or opening 306 to permit observation of the test specimen and stirring element 104 during testing. Since heater jacket 304 covers heating element 302, the only portion of heating element 302 that is visible in FIG. 3 is the part that wraps around the back of the test vessel 102 and is visible through opening 306. In an alternative preferred embodiment, the heater jacket covers the bottom of the test vessel 102 and the bottom portion of the heater jacket may have a reflective inner surface.

Heater jacket 304 is designed to provide a gap between the outer surface of heating element 302 and the inner surface of heater jacket 304. The gap permits more accurate temperature control. Heating element 302 is powered and controlled via wiring 308 by controller 112 of FIG. 1.

Figure 4:
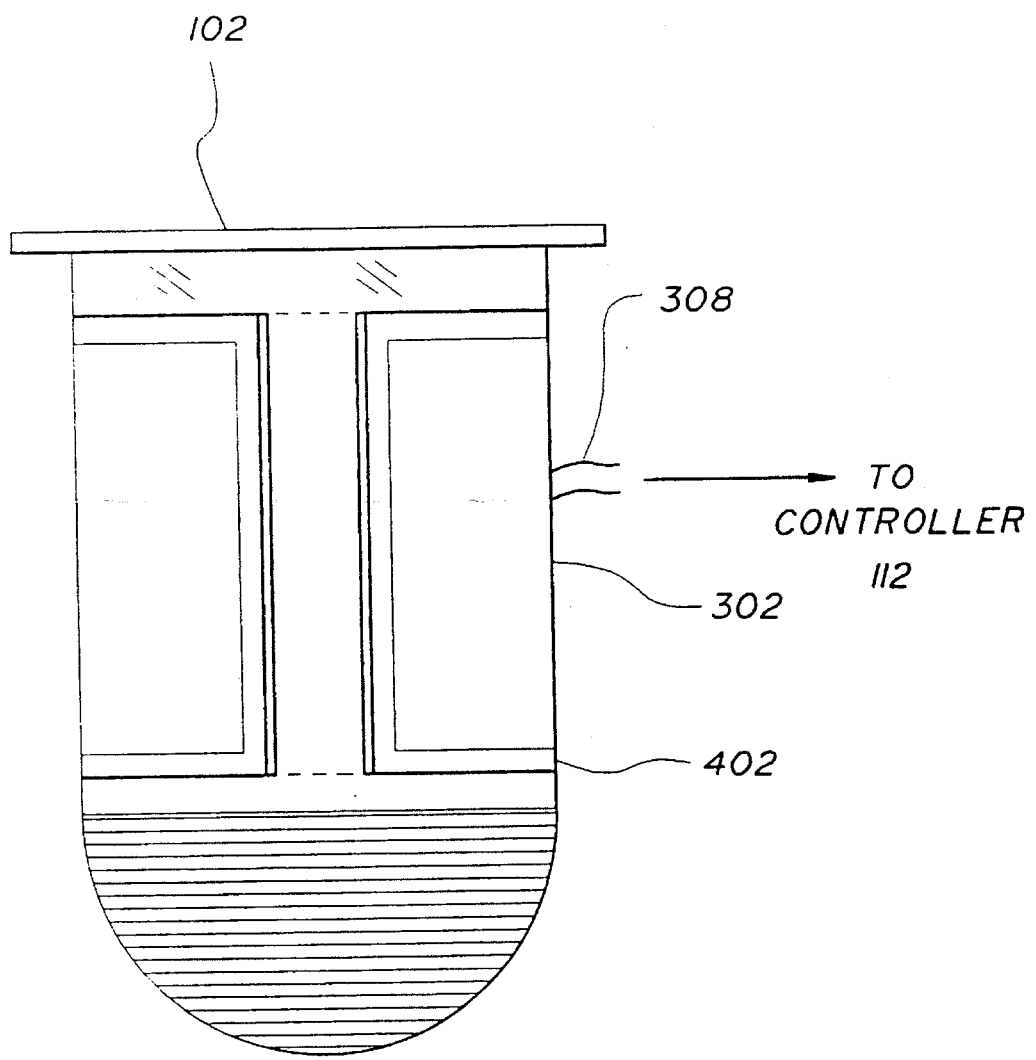
FIG. 4 shows a front view of a test vessel with an alternative preferred configuration of a heater jacket used to hold the heating element onto the test vessel.

Referring now to FIG. 4, there is shown a test vessel 102 with an alternative preferred configuration of a heater jacket 402 used to hold the heating element 302 onto test vessel 102. Heater jacket 402 is a spring-loaded stainless steel open frame that provides a border over the outer edges of heating element 302. In this embodiment, most of the outer surface of heating element 302 is uncovered and exposed to the air to permit accurate temperature control.

Figure 5:
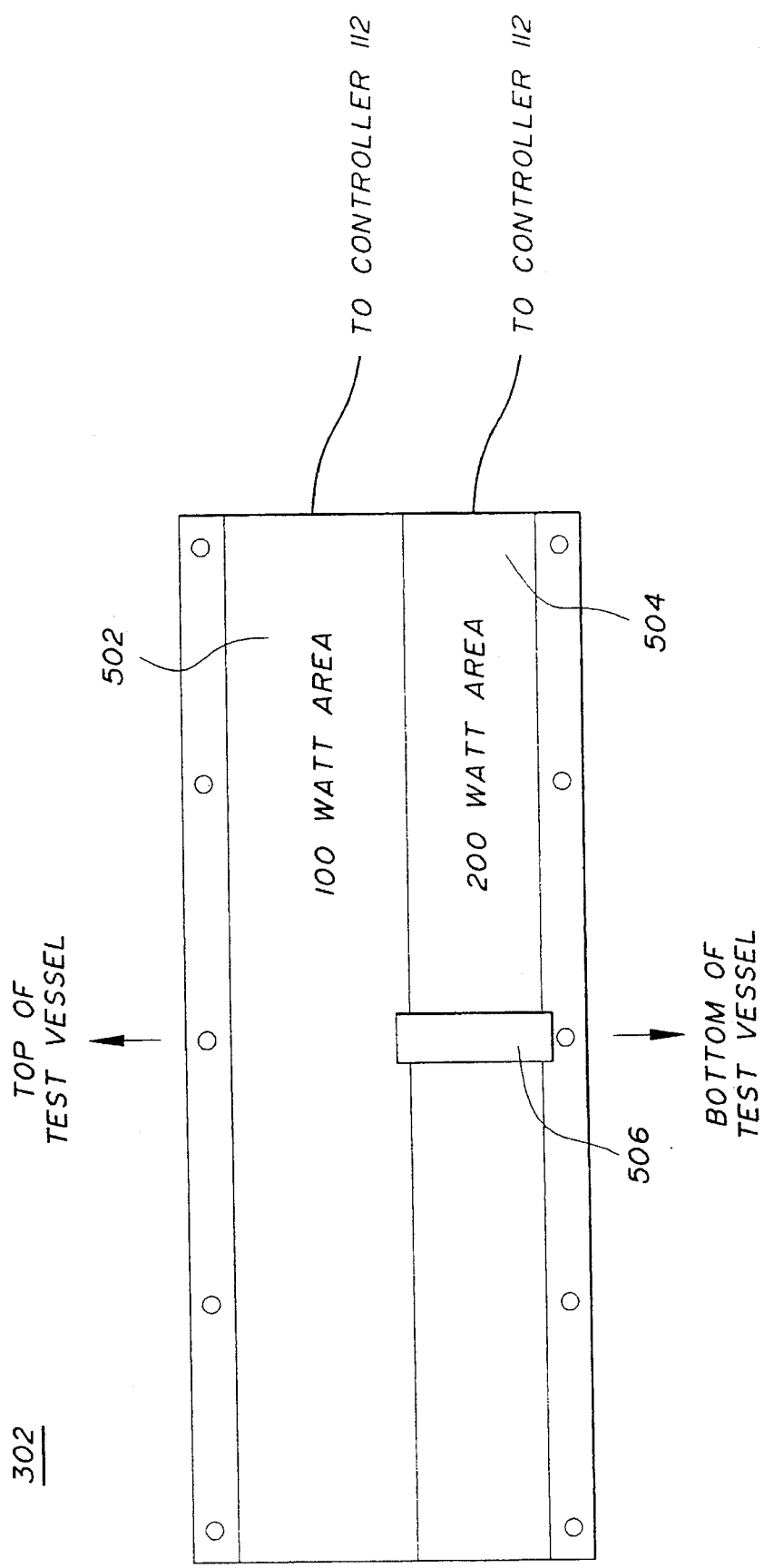
FIG. 5 is a plan view of a heating element of the test vessels of FIGS. 3 and 4, before the heating element is wrapped around the test vessel.

Referring now to FIG. 5, there is shown a plan view of heating element 302 of FIGS. 3 and 4, before the heating element is wrapped around test vessel 102, according to a preferred embodiment of the present invention. Heating element 302 is a flexible resistive heating device such as an etched foil silicone rubber band heater. Heating element 302 has a silicone side and a fiberglass support side. In order to permit easy installation of heating element 302 around test vessel 102, the low-friction fiberglass side faces the test vessel rather than the high-friction silicone side.

As shown in FIG. 5, heating element 302 has two heating areas with different power ratings: a 100-watt area 502 and a 200-watt area 504. When wrapped around test vessel 102, the 100-watt area 502 is closer to the top of test vessel 102 and the 200-watt area 504 is closer to the bottom of test vessel 102, as indicated in FIG. 5. Heating areas 502 and 504 are powered by controller 112 of FIG. 1 via wiring 308.

Heating areas 502 and 504 may be configured to be powered at different voltages, such as 115 or 230 volts. Controller 112 is preferably capable of powering heating element 302 at varying power levels from 0 to 300 watts. In addition, 200-watt area 504 has a thermal fuse 506 that trips at a designed temperature limit, such as about 180 degrees Fahrenheit, to prevent a run-away temperature scenario.

In an alternative preferred embodiment of heating element 302, the controller is capable of powering each heating area independently at varying power levels from 0 to about 100 watts for area 502 and from 0 to about 200 watts for area 504. Those skilled in the art will understand that, under such an embodiment, when, for example, a 1-liter test vessel 102 is filled with only 500 milliliters of test solution, 100-watt area 502 need not be powered to control the temperature of the test solution.

Those skilled in the art will understand that alternative embodiments of heating element 302 fall within the scope of the present invention. For example, the heating elements may be constructed of different materials such as Kapton®, manufactured by E. I. DuPont de Nemours of Wilmington, Del., instead of silicone. In addition, the heating areas 502 and 504 may have power ratings of other than 100 and 200 watts, respectively. In general, heating element 302 may be any device for heating a test solution in a test vessel 102. For example, heating element 302 may comprise a metal block, such as an aluminum block, with embedded heaters, such as resistive heaters. Heating element 302 specifically is not a water (or other liquid) bath that heats a test solution within a test vessel by immersing the test vessel in the bath. One purpose of heating element 302 is to eliminate the need for a water bath in dissolution testing apparatuses.

Figure 6:
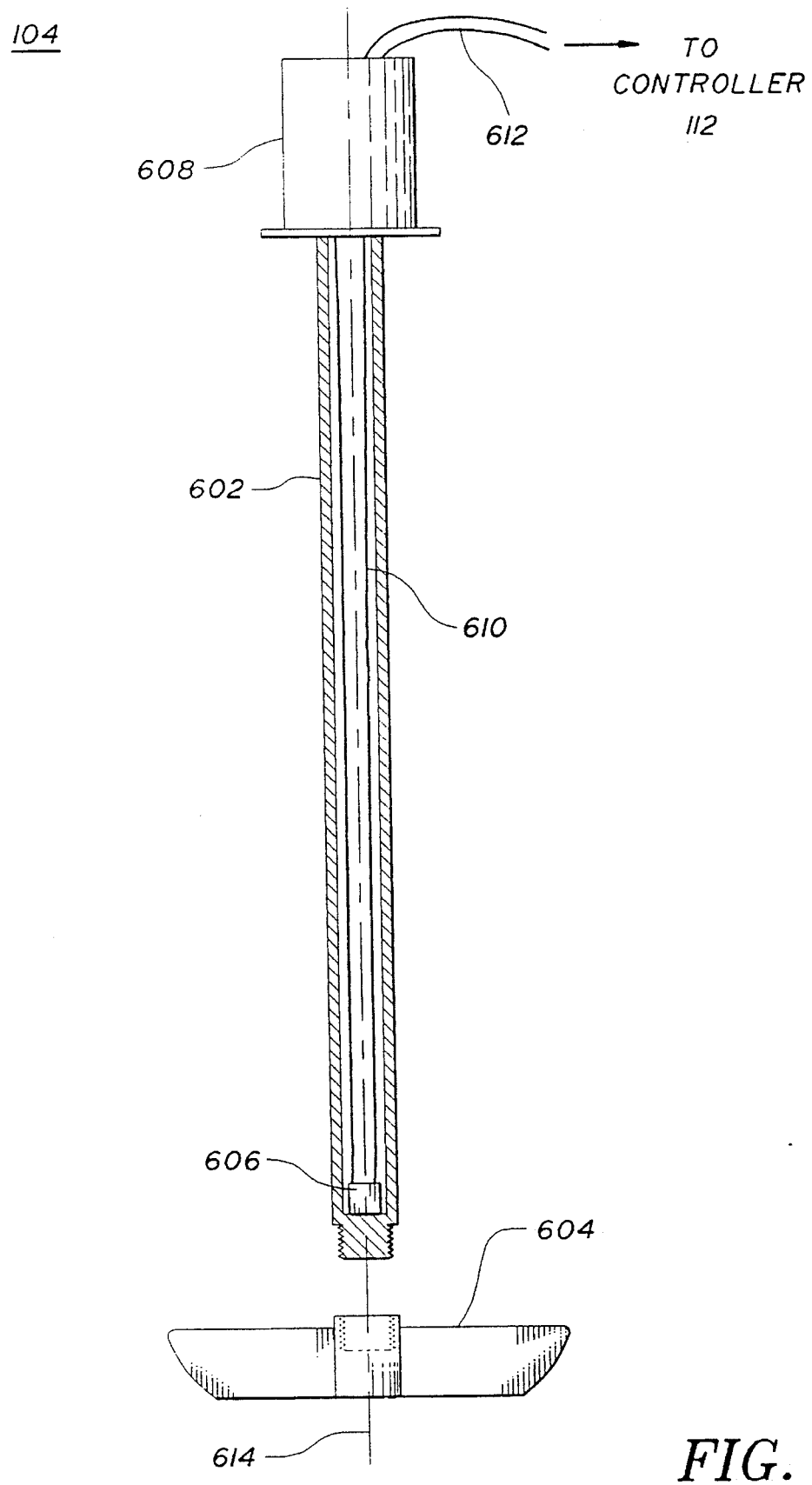
FIG. 6 shows an exploded, partial cutaway front view of a paddle-type stirring element of the apparatus of FIG. 1.

Referring now to FIG. 6, there is shown an exploded, partial cutaway front view of paddle-type stirring element 104 of apparatus 100 of FIG. 1. Paddle-type stirring element 104 comprises hollow shaft 602, blade 604, temperature sensor 606, and signal transfer device 608. Shaft 602 and blade 604 are appropriately threaded and tapped to permit them to be removably coupled to form a leak-proof seal. In a preferred embodiment, an O-ring seal (not shown) is used, although other types of seals may alternatively be employed. Temperature sensor 606 is located near the bottom of hollow shaft 602 and is preferably in physical thermal contact with the inner surface of shaft 602. Power to temperature sensor 606 and signals from temperature sensor 606 are transmitted along cable 610. Cable 610 is in turn electrically coupled to signal transfer device 608 which transfers power and signals between cable 610 and cable 612. Those skilled in the art will understand that signal transfer device 608 provides transfer of power and signals when stirring element 104 is rotated about shaft axis 614 with respect to cable 612. Cable 612 is in turn connected to the same controller 112 that controls the power to the heating element 302 of test vessel 102 of FIG. 3.

Figure 7:
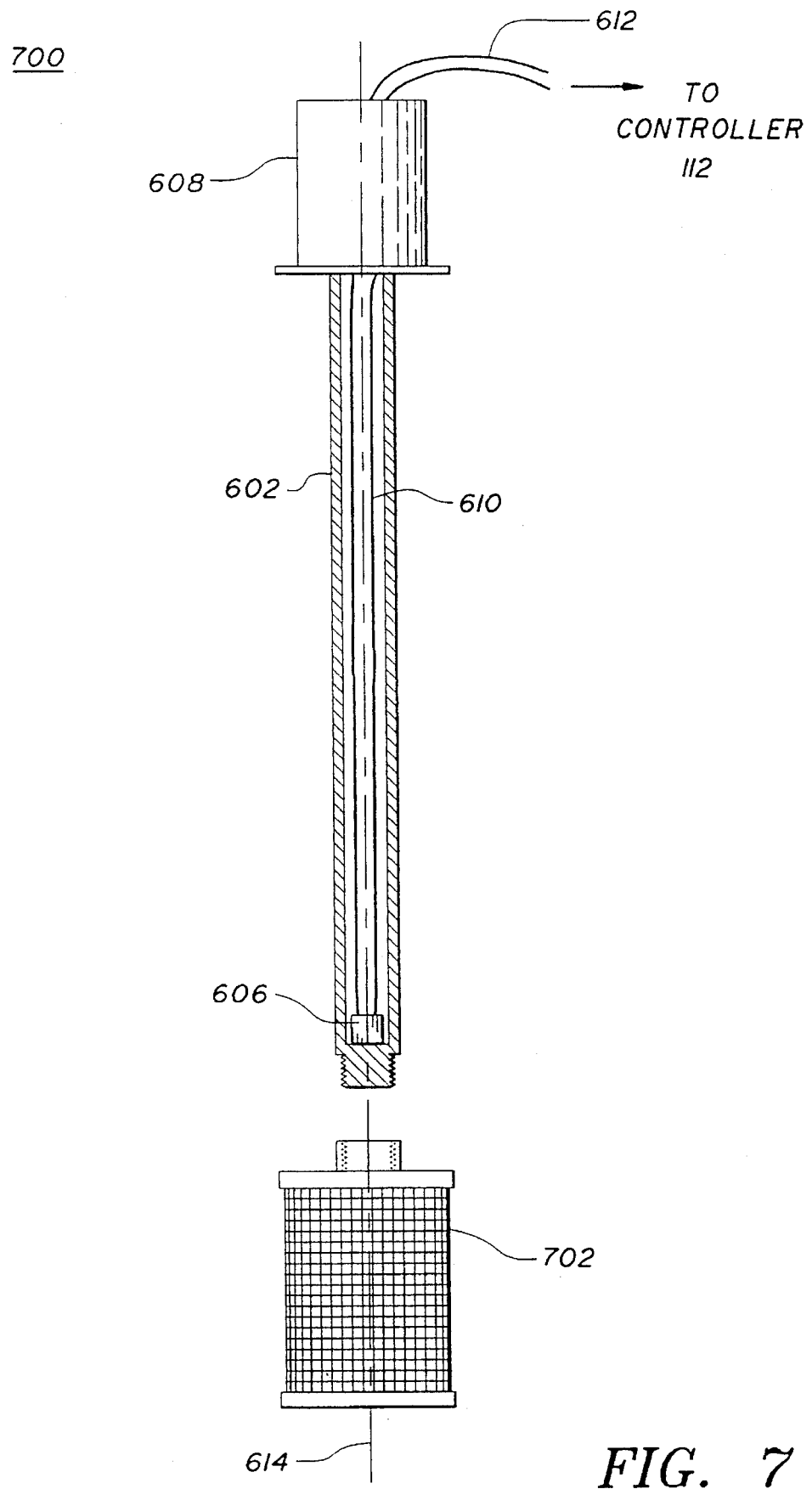
FIG. 7 shows an exploded, partial cutaway front view of a basket-type stirring element of the apparatus of FIG. 1.

Referring now to FIG. 7, there is shown an exploded, partial cutaway front view of basket-type stirring element 700, according to a preferred embodiment of the present invention. Those skilled in the art will understand that dissolution testing may be performed using basket-type stirring element 700 in place of paddle-type stirring element 104 of FIG. 6. Basket-type stirring element 700 is preferably identical to paddle-type stirring element 104, except that blade 604 of FIG. 6 is replaced by basket 702. Basket 702 is tapped similarly to blade 604 to permit removable coupling to hollow shaft 602. As a result, blade 604 and basket 702 are interchangeable attachments to a common shaft 602.

Figure 8:
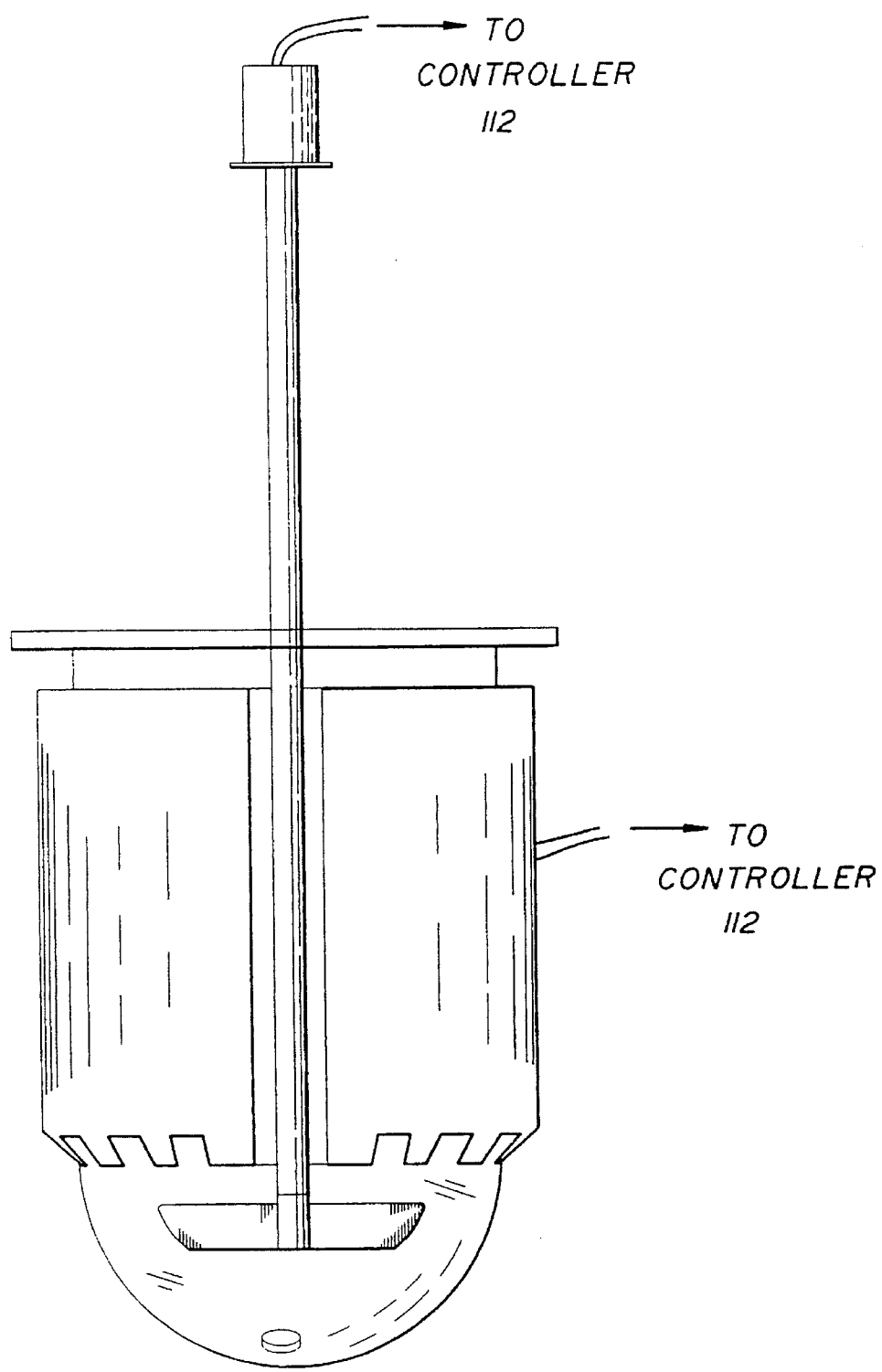
FIGS. 8 and 9 show the assembled paddle-type and basket-type stirring elements of FIGS. 6 and 7, respectively, positioned within test vessels for dissolution testing.
Figure 9:
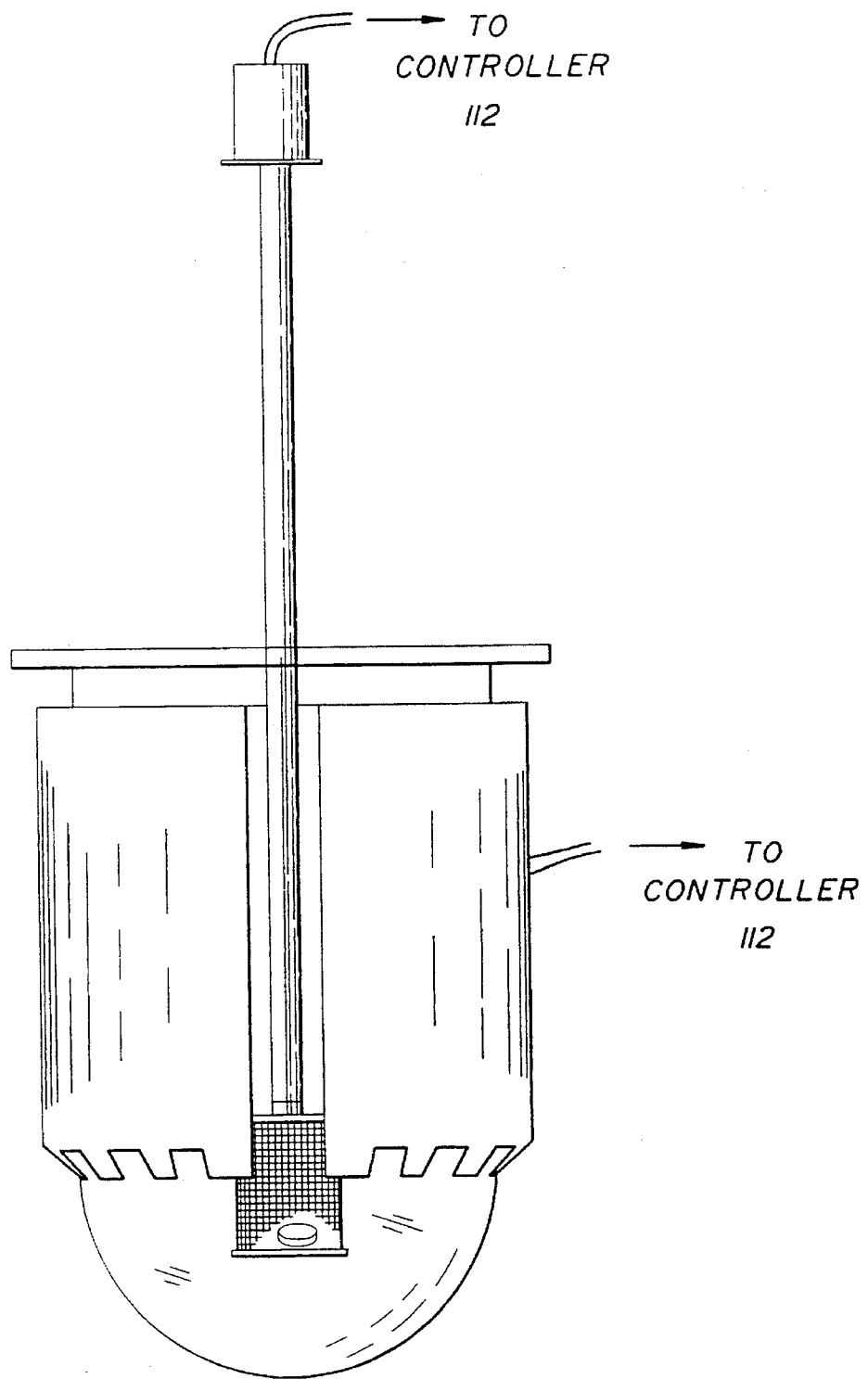

Each stirring element 104 of apparatus 100 of FIG. 1 may be individually configured to perform dissolution testing as either a paddle-type stirring element or a basket-type stirring element by installing the appropriate blade or basket attachment. FIGS. 8 and 9 show the assembled paddle-type and basket-type stirring elements, respectively, positioned within test vessels for dissolution testing.

The sizes, shapes, and materials of test vessel 102 of FIG. 2, shaft 602 and blade 604 of FIG. 6, and basket 702 of FIG. 7 are preferably selected to conform with the appropriate USP regulations. As such, alternative preferred embodiments of those elements are those permitted by USP regulations.

Temperature sensor 606 may be any suitable device for generating signals representative of temperature and is preferably a resistance temperature detector (RTD). It will be understood that, in alternative preferred embodiments, temperature sensor 606 may be other devices such as thermocouple or thermistor devices.

Signal transfer device 608 may be any suitable device for transmitting electrical energy to and from rotating equipment, such as a mercury rotating electrical connector sold by Mercotac Inc. of Carlsbad, Calif. or a slip ring assembly sold by Airflyte Electronics Company of Bayonne, N.J.

In an alternative preferred embodiment of the stirring elements of the present invention, each stirring element comprises a hollow shaft with an inner stationary probe. In this embodiment, the probe does not rotate when the shaft is rotated to stir the test solution. Those skilled in the art will understand that an energy transfer device such as a slip ring assembly is not required for this alternative embodiment. As a result, this embodiment avoids any of the possible drawbacks associated with the cost and potentially limited lifetime of slip ring assemblies.

Figure 13:
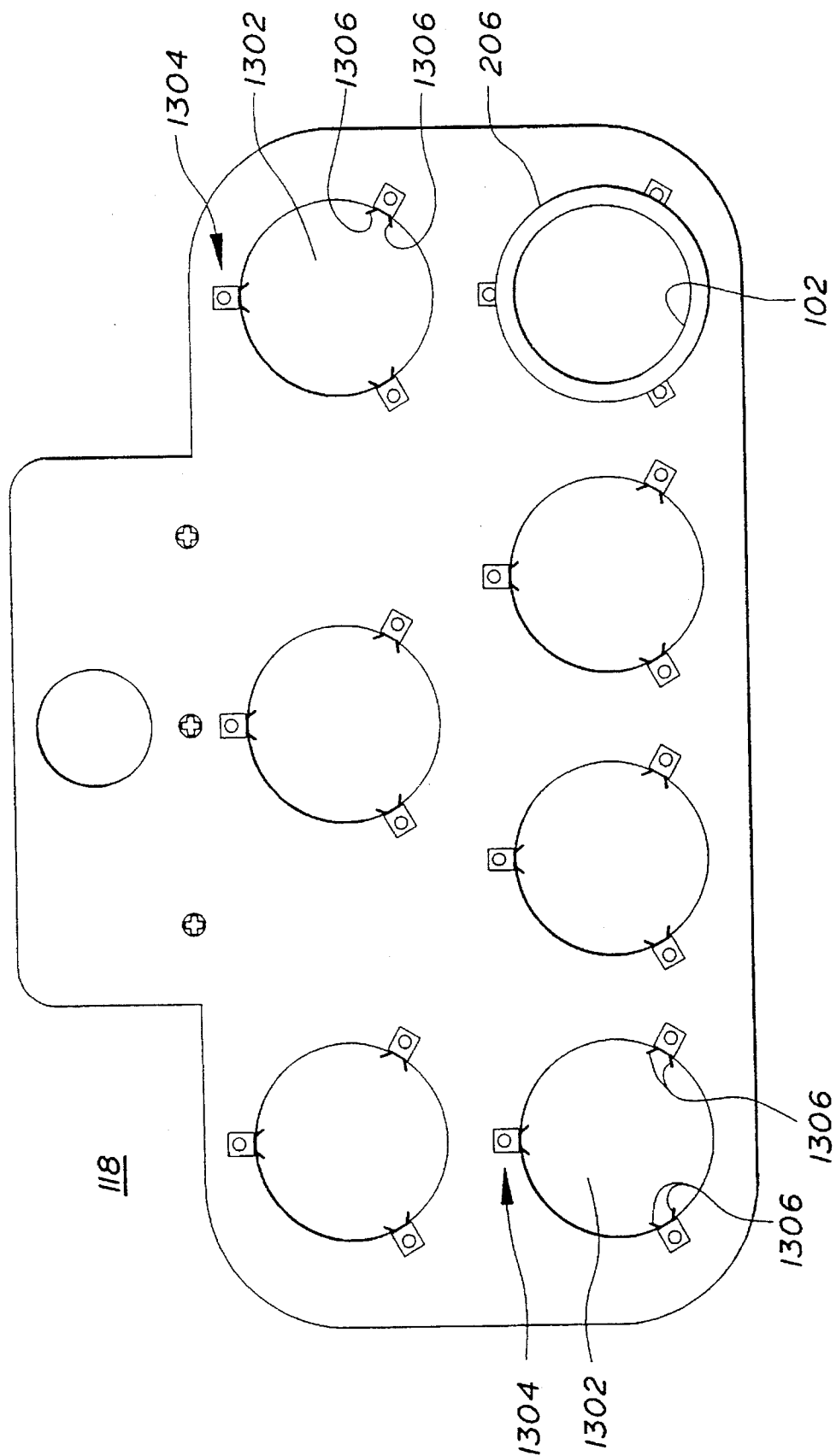
FIG. 13 is a plan view of the test vessel holding plate of FIG. 1.

Referring now to FIG. 13, there is shown a plan view of the test vessel holding plate 118 of apparatus 100 of FIG. 1, according to a preferred embodiment of the present invention. Holding plate 118 has seven openings 1302, one for each test vessel. Each opening 1302 has three alignment fixtures 1304 positioned around the circumference of the opening preferably with about 120 degrees separation. Each alignment fixture 1304 has two alignment arms 1306, which extend into the area of the opening or just above the opening. The alignment arms 1306 are made of a semi-rigid material, such as PVC plastic.

Holding plate 118 provides at least two functions: (1) supporting the weight of the test vessels and (2) aligning the test vessels under the stirring elements 104. The flange 206 of a test vessel rests on top of the alignment fixtures 1304, thereby providing support for the weight of the test vessel. All six centering arms 1306 of the three alignment fixtures 1304 of an opening 1302 are preferably in contact with the OD of the cylindrical portion 202 of the test vessel. Altogether the centering arms 1306 exert compressive forces that tend to center the test vessel within the opening. In this way, the test vessel may be aligned with respect to the corresponding stirring element 104. Those skilled in the art will understand that the three alignment fixtures provide symmetrical spring forces on the test vessel to align the test vessel and hold it in place during dissolution testing.

Figure 10:
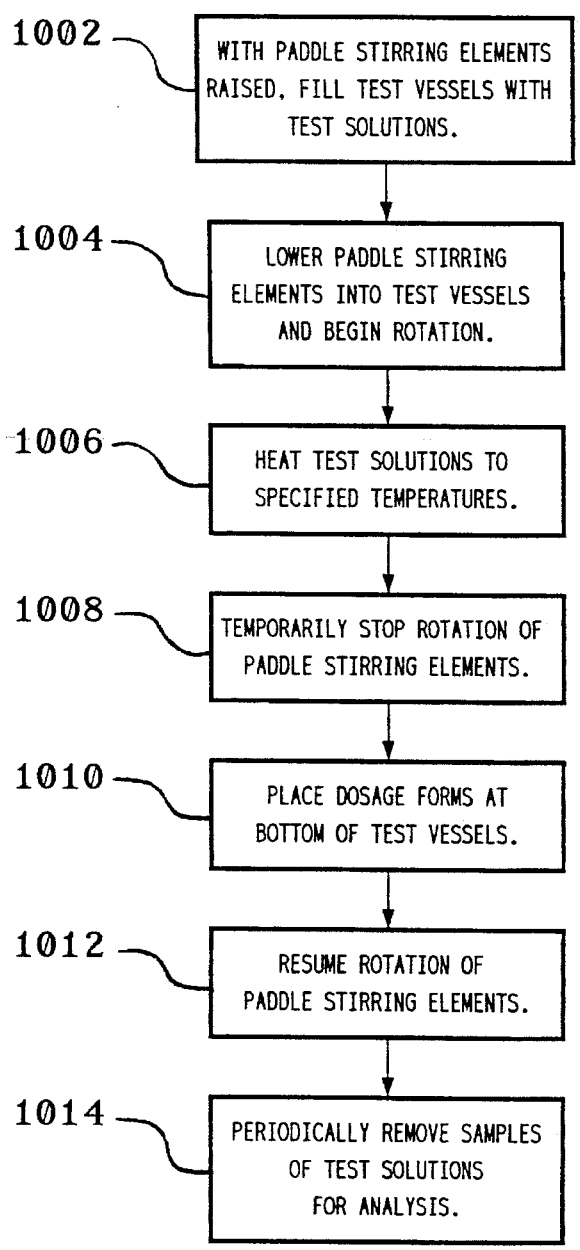
FIG. 10 is a process flow diagram for a typical dissolution test using the apparatus of FIG. 1 configured with paddle-type stirring elements.

Referring now to FIG. 10, there is shown a process flow diagram for a typical dissolution test using apparatus 100 of FIG. 1 configured with paddle-type stirring elements 104. With the paddle-type stirring elements 104 raised (i.e., not inserted into test vessels 102), the test vessels 102 are filled with the appropriate test solutions (block 1002 of FIG. 10). The paddle-type stirring elements 104 are then lowered into test vessels 102 and rotated to stir the test solutions (block 1004). With the paddle-type stirring elements 104 rotating, the test solutions are heated to the specified temperatures using heating elements 302 of FIG. 3 (block 1006). Controller 112 of apparatus 100 is preferably able to control the temperature of the test solution in each test vessel 102 independently of the other test solution temperatures.

After the desired test solution temperatures have been achieved, the rotation of the paddle-type stirring elements 104 is temporarily stopped (block 1008) and the dosages are placed at the bottom of the test vessels 102 (block 1010). The rotation of the paddle-type stirring elements 104 is then resumed at specified rates for specified durations (block 1012) to begin the actual dissolution testing.

Throughout the dissolution testing procedure, samples of the test solutions may be periodically removed for analysis to determine the degree of dissolution of the dosages (block 1014). Those skilled in the art will understand that such sampling may be accomplished manually by syringe or pipet or via auxiliary automatic sampling system known in the art.

Figure 11:
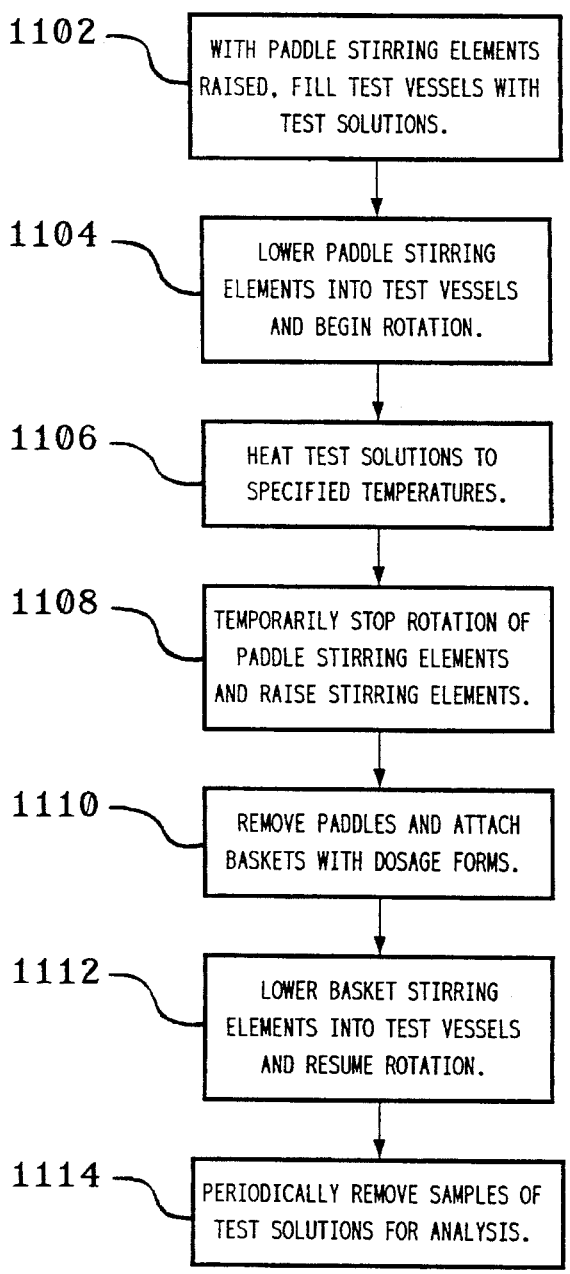
FIG. 11 is a process flow diagram for a typical dissolution test using the apparatus of FIG. 1 configured with basket-type stirring elements.

Referring now to FIG. 11, there is shown a process flow diagram for a typical dissolution test using apparatus 100 of FIG. 1 configured with basket-type stirring elements 700. Basket-type dissolution testing begins with the stirring elements configured at paddle-type stirring elements 104. With the paddle-type stirring elements 104 raised (i.e., not inserted into test vessels 102), the test vessels 102 are filled with the appropriate test solutions (block 1102 of FIG. 11). The paddle-type stirring elements 104 are then lowered into test vessels 102 and rotated to stir the test solutions (block 1104). With the paddle-type stirring elements 104 rotating, the test solutions are heated to the specified temperatures using heating elements 302 of FIG. 3 (block 1106).

After the desired test solution temperatures have been achieved, the rotation of the paddle-type stirring elements 104 is temporarily stopped and the stirring elements are raised out of the test solutions (block 1108). The paddle attachments are then replaced with basket attachments containing the appropriate dosages (block 1110). The basket-type stirring elements 700 are then lowered into the test vessels 102 and rotated at specified rates for specified durations (block 1112) to begin the actual dissolution testing.

As in paddle-type dissolution testing, throughout the basket-type dissolution testing procedure, samples of the test solutions may be periodically removed for analysis to determine the degree of dissolution of the dosages (block 1114).

Throughout both the dissolution test procedures of FIGS. 10 and 11, controller 112 independently controls the temperature of each of the test solutions using temperature measurements from temperature sensors 606 and by powering heating elements 302. Dissolution testing with apparatus 100 may be performed with some of the stirring elements configured as paddle-type stirring elements and other stirring elements configured as basket-type stirring elements. In an alternative preferred embodiment of apparatus 100, controller 112 may independently control the rate and duration of rotation of each of the stirring elements.

The controller 112 of apparatus 100 simultaneously controls the temperatures of all of the solutions within the test vessels 102. The controller is preferably a microprocessor-based controller that implements a closed-loop proportional integral derivative (PID) control algorithm using the signals from the temperature sensors 606 as the feedback signals to control the power to the heating elements 302 to achieve and maintain the desired test solution temperatures for each of the test vessels.

Figure 12:
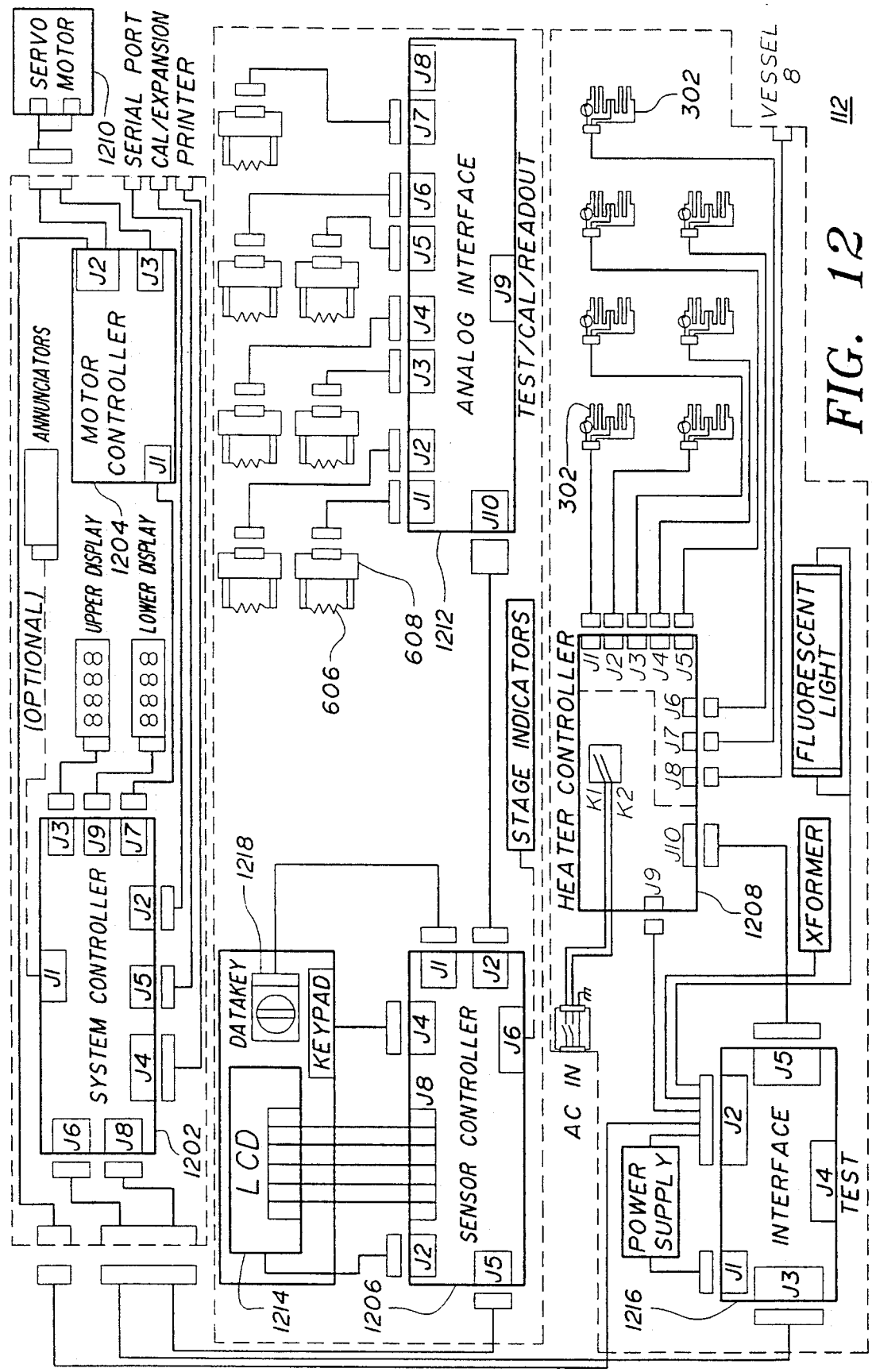
FIG. 12 is a circuit block diagram of the controller of the apparatus of FIG. 1.

Referring now to FIG. 12, there is shown a circuit block diagram of controller 112 of apparatus 100 of FIG. 1, according to a preferred embodiment of the present invention. Controller 112 has a system controller 1202, a motor controller 1204, a sensor controller 1206, and a heater controller 1208. Motor controller 1204 controls the operations of the servo motor 1210, which raises, lowers, and rotates the stirring elements 104.

Sensor controller 1206 processes the signals received from the shaft-mounted RTD temperature sensors 606 via the signal transfer devices 608 and the RTD signal analog interface 1212. Sensor controller 1206 also controls the display of the test solution temperatures on liquid crystal display (LCD) device 1214. LCD device 1214 may also be used to display the power levels to the heating elements 302. The display is preferably an LCD display but may alternatively be other types of displays such as an LED display.

Heater controller 1208 controls the power distributed to the heating areas of the heating elements 302. Heater controller 1208 interfaces with system controller 1202 via interface 1216.

System controller 1202 monitors and controls the operations of motor controller 1204, sensor controller 1206, and heater controller 1208. System controller 1202 also provides the capability to print the dissolution test results (e.g., temperature profiles) for all of the test vessels on a single printer.

Controller 112 is configured with a user-accessible, non-volatile, removable memory device (such as datakey 1218 of FIG. 12). The system configuration and test setup parameters (e.g., temperatures, stirring element speeds, sampling intervals, infinity RPM, drug name) may be entered into the removable memory device by the user, or the removable device may be supplied pre-configured to the user. The memory device helps achieve consistent test runs by eliminating possible errors in test results caused by improper system setup.

Controller 112 implements a heater safety procedure to turn off the heater elements 302 automatically if a problem arises in the apparatus that could cause a thermal runaway condition. Heater controller 1208 is configured to accept a periodic signal from system controller 1202. This signal contains on/off control information for each heating element 302. If a hardware problem occurs that prevents this periodic signal from arriving at heater controller 1208, or if the normal operation of system controller 1202 is interrupted, then all heating elements 302 are automatically turned off.

Controller 112 also provides heater burnout/sensor open detection. Controller 112 continually monitors the status of each heating element 302 and each temperature sensor 606. If a problem arises, then appropriate action is taken to prevent a thermal runaway condition. The rate of change of temperature is detected for each test vessel 102. If a heating element 302 fails to warm the corresponding vessel 102 to the desired temperature, then appropriate action is taken. Controller 112 also monitors the state of the temperature sensors 606. If a sensor 606 develops a short, or an open, then appropriate action is taken.

Those skilled in the art will appreciate the advantages of apparatus 100 of the present invention over conventional dissolution testing apparatuses. One advantage is the elimination of the water bath and its associated water pump/heater assembly. This alleviates the problems associated with leaking, evaporation, algae growth, emptying, cleaning, and refilling of the water bath. Moreover, the time required to heat the test solutions to the specified temperatures with apparatus 100 is typically less than that of conventional dissolution testing apparatuses having water baths. Furthermore, the use of a hollow stainless steel shaft 602 instead of the conventional solid stainless steel shaft results in less temperature loss with a cold shaft is inserted into a warm test solution at the start of dissolution testing.

Another advantage of apparatus 100 is that the temperature sensors within the hollow stirring elements provides the capability for direct in situ temperature measurements of the test solutions during test procedures without having to interrupt the test procedures.

Another advantage of apparatus 100 that was mentioned earlier is that the temperature of each test solution may be independently monitored and controlled during a single test procedure. Apparatus 100 may also be configured to perform dissolution testing with paddle-type stirring elements in some test vessels and basket-type stirring elements in other test vessels.

Those skilled in the art will understand that the dissolution testing apparatuses of the present invention may be used to perform dissolution tests on materials other than pharmaceutical dosages.

It will be further understood that various changes in the details, materials, and arrangements of the parts which have been described and illustrated in order to explain the nature of this invention may be made by those skilled in the art without departing from the principle and scope of the invention as expressed in the following claims.

What is claimed is:

1. An apparatus for dissolution testing of a material in a test solution within a test vessel, comprising:

(a) a stirring element for stirring the test solution;

(b) a non-liquid-bath heating element placed around the outside of the test vessel for heating the test solution; and (c) a controller for controlling the heating element to control the temperature of the test solution, wherein the stirring element comprises:

(1) a hollow shaft; and (2) a temperature sensor located within the hollow shaft for generating signals representative of the temperature of the test solution when the hollow shaft is inserted into the test solution, wherein the controller controls the heating element in accordance with the signals from the temperature sensor.

2. The apparatus of claim 1, wherein the test vessel comprises a reflective coating applied to a surface of the test vessel.

3. The apparatus of claim 1, wherein the stirring element further comprises:

(3) a signal transfer device for transmitting the signals from the temperature sensor to the controller while the stirring element stirs the test solution.

4. The apparatus of claim 1, wherein the stirring element comprises:

(1) a shaft adapted to be removably coupled to a plurality of different stirring element attachments.

5. The apparatus of claim 4, wherein the plurality of different stirring element attachments comprises a blade attachment and a basket attachment.

6. The apparatus of claim 1, further comprising:

(d) a heater jacket surrounding the heating element for holding the heating element in place around the test vessel.

7. The apparatus of claim 6, wherein the heater jacket and heating element are configured to permit viewing of the stirring element through the front of the test vessel when the stirring element is inserted into the test vessel.

8. The apparatus of claim 6, wherein the heater jacket and heating element are configured to provide a gap between the outer surface of the heating element and the inner surface of the heater jacket.

9. The apparatus of claim 1, wherein the heating element comprises:

(1) a first heating area having a first power rating; and (2) a second heating area having a second power rating different from the first power rating.

10. An apparatus for dissolution testing of a material in a test solution within a test vessel, comprising:

(a) a stirring element for stirring the test solution, wherein the stirring element comprises:

(1) a hollow stirring assembly; and (2) a temperature sensor located within the hollow stirring assembly for generating signals representative of the temperature of the test solution, wherein the hollow stirring assembly comprises:

(1) a hollow shaft adapted to be removably coupled to a plurality of different stirring element attachments.

11. The apparatus of claim 10, wherein the test vessel comprises a reflective coating applied to a surface of the test vessel.

12. The apparatus of claim 10, wherein the stirring element further comprises:

(3) a signal transfer device for transmitting the signals from the temperature sensor while the stirring element stirs the test solution.

13. The apparatus of claim 10, wherein the plurality of different stirring element attachments comprises a blade attachment and a basket attachment.

14. The apparatus of claim 10, further comprising:

(b) a heating element placed around the outside of the test vessel for heating the test solution; and (c) a controller for controlling the heating element to control the temperature of the test solution in accordance with the signals from the temperature sensor.

15. The apparatus of claim 14, further comprising:

(d) a heater jacket surrounding the heating element for holding the heating element in place around the test vessel.

16. The apparatus of claim 15, wherein the heater jacket and heating element are configured to permit viewing of the stirring element through the front of the test vessel when the stirring element is inserted into the test vessel.

17. The apparatus of claim 15, wherein the heater jacket and heating element are configured to provide a gap between the outer surface of the heating element and the inner surface of the heater jacket.

18. The apparatus of claim 14, wherein the heating element comprises:

(1) a first heating area having a first power rating; and
(2) a second heating area having a second power rating different from the first power rating.

19. An apparatus for dissolution testing of a material in a test solution, comprising:

(a) a test vessel for holding the test solution and the material, wherein the test vessel comprises a reflective coating applied to a surface of the test vessel; and (b) a stirring element for stirring the test solution, wherein the stirring element comprises:
(1) a hollow shaft; and
(2) a temperature sensor located within the hollow shaft for generating signals representative of the temperature of the test solution.

20. The apparatus of claim 19, wherein the stirring element further comprises:

(3) a signal transfer device for transmitting the signals from the temperature sensor while the stirring element stirs the test solution.

21. The apparatus of claim 19, wherein the stirring element comprises:

(1) a shaft adapted to be removably coupled to a plurality of different stirring element attachments.

22. The apparatus of claim 21, wherein the plurality of different stirring element attachments comprises a blade attachment and a basket attachment.

23. The apparatus of claim 19, further comprising:

(c) a heating element placed around the outside of the test vessel for heating the test solution; and (d) a controller for controlling the heating element to control the temperature of the test solution.

24. The apparatus of claim 23, further comprising:

(e) a heater jacket surrounding the heating element for holding the heating element in place around the test vessel.

25. The apparatus of claim 24, wherein the heater jacket and heating element are configured to permit viewing of the stirring element through the front of the test vessel when the stirring element is inserted into the test vessel.

26. The apparatus of claim 24, wherein the heater jacket and heating element are configured to provide a gap between the outer surface of the heating element and the inner surface of the heater jacket.

27. The apparatus of claim 23, wherein the heating element comprises:

(1) a first heating area having a first power rating; and
(2) a second heating area having a second power rating different from the first power rating.

28. An apparatus for dissolution testing of a material in a test solution within a test vessel, comprising:

(a) a stirring element for stirring the test solution, wherein the stirring element comprises:
(1) a shaft adapted to be removably coupled to a plurality of different stirring element attachments;

(b) a heating element placed around the outside of the test vessel for heating the test solution; and (c) a controller for controlling the heating element to control the temperature of the test solution, wherein the heating element comprises:
(1) a first heating area having a first power rating; and
(2) a second heating area having a second power rating different from the first power rating.

29. The apparatus of claim 28, wherein the shaft is hollow and the stirring element further comprises a temperature sensor located within the hollow shaft for generating signals representative of the temperature of the test solution.

30. The apparatus of claim 29, wherein the stirring element further comprises a signal transfer device for transmitting the signals from the temperature sensor while the stirring element stirs the test solution.

31. The apparatus of claim 28, wherein the test vessel comprises a reflective coating applied to a surface of the test vessel.

32. The apparatus of claim 28, wherein the plurality of different stirring element attachments comprises a blade attachment and a basket attachment.

33. The apparatus of claim 28, further comprising:

(d) a heater jacket surrounding the heating element for holding the heating element in place around the test vessel.

34. The apparatus of claim 33, wherein the heater jacket and heating element are configured to permit viewing of the stirring element through the front of the test vessel when the stirring element is inserted into the test vessel.

35. The apparatus of claim 33, wherein the heater jacket and heating element are configured to provide a gap between the outer surface of the heating element and the inner surface of the heater jacket.

36. An apparatus for dissolution testing of a material in a test solution within a test vessel, comprising:

(a) a stirring element for stirring the test solution; and (b) a holding plate having at least one opening for receiving and supporting the test vessel, the holding plate comprising a plurality of alignment fixtures for aligning the test vessel with respect to the stirring element.

37. The apparatus of claim 36, wherein each alignment fixture comprises two semi-rigid alignment arms adapted to provide compressive force to the test vessel.

38. The apparatus of claim 36, wherein the holding plate comprises three alignment fixtures for each opening.

39. The apparatus of claim 36, wherein the stirring element comprises:

(1) a shaft; and
(2) a stirring element attachment, adapted to be removably coupled to the shaft.

40. The apparatus of claim 39, wherein the shaft is hollow and the stirring element further comprises a temperature sensor located within the hollow shaft for generating signals representative of the temperature of the test solution.

41. The apparatus of claim 40, wherein the stirring element further comprises a signal transfer device for transmitting the signals from the temperature sensor while the stirring element stirs the test solution.

42. The apparatus of claim 36, wherein the test vessel comprises a reflective coating applied to a surface of the test vessel.

43. The apparatus of claim 36, further comprising:
(c) a heating element placed around the outside of the test vessel for heating the test solution; and
(d) a controller for controlling the heating element to control the temperature of the test solution.

44. The apparatus of claim 43, further comprising:
(e) a heater jacket surrounding the heating element for holding the heating element in place around the test vessel.

45. The apparatus of claim 44, wherein the heater jacket and heating element are configured to permit viewing of the stirring element through the front of the test vessel when the stirring element is inserted into the test vessel.

46. The apparatus of claim 44, wherein the heater jacket and heating element are configured to provide a gap between the outer surface of the heating element and the inner surface of the heater jacket.

47. The apparatus of claim 43, wherein the heating element comprises:
(1) a first heating area having a first power rating; and
(2) a second heating area having a second power rating different from the first power rating.

48. An apparatus for dissolution testing of a plurality of materials in a plurality of test solutions within a plurality of test vessels, comprising:
(a) a stirring element for each test vessel, for stirring the test solution, wherein each stirring element comprises:
(1) a hollow shaft;
(2) a stirring element attachment, adapted to be removably coupled to the hollow shaft, wherein the stirring element attachment is one of a blade attachment and a basket attachment;
(3) a temperature sensor located within the hollow shaft for generating signals representative of the temperature of the test solution when the hollow shaft is inserted into the test solution; and
(4) a signal transfer device for transmitting the signals from the temperature sensor while the stirring element stirs the test solution;
(c) a heating element for each test vessel, placed around the outside of the test vessel for heating the test solution, wherein the heating element comprises:
(1) a first heating area having a first power rating; and
(2) a second heating area having a second power rating different from the first power rating;
(d) a heater jacket for each test vessel, surrounding the heating element for holding the heating element in place around the test vessel, wherein the heater jacket and heating element are configured to permit viewing of the stirring element through the front of the test vessel when the stirring element is inserted into the test vessel and wherein the heater jacket and heating element are configured to provide a gap between the outer surface of the heating element and the inner surface of the heater jacket;
(e) a controller for controlling each heating element to control the temperature of each test solution in accordance with the signals from each temperature sensor.

49. An apparatus for dissolution testing of a material in a test solution within a test vessel, comprising:
(a) a stirring element for stirring the test solution;
(b) a heating element placed around the outside of the test vessel for heating the test solution; and
(c) a controller for controlling the heating element to control the temperature of the test solution, wherein the stirring element comprises:
(1) a hollow shaft; and
(2) a temperature sensor located within the hollow shaft for generating signals representative of the temperature of the test solution when the hollow shaft is inserted into the test solution, wherein the controller controls the heating element in accordance with the signals from the temperature sensor.

50. The apparatus of claim 49, wherein the stirring element further comprises:
(3) a signal transfer device for transmitting the signals from the temperature sensor to the controller while the stirring element stirs the test solution.

51. The apparatus of claim 49, further comprising:
(d) a heater jacket surrounding the heating element for holding the heating element in place around the test vessel.

52. The apparatus of claim 51, wherein the heater jacket and heating element are configured to permit viewing of the stirring element through the front of the test vessel when the stirring element is inserted into the test vessel.

53. The apparatus of claim 51, wherein the heater jacket and heating element are configured to provide a gap between the outer surface of the heating element and the inner surface of the heater jacket.

54. The apparatus of claim 49, wherein the heating element comprises:
(1) a first heating area having a first power rating; and
(2) a second heating area having a second power rating different from the first power rating.

55. An apparatus for dissolution testing of a material in a test solution within a test vessel, comprising:
(a) a stirring element for stirring the test solution;
(b) a heating element placed around the outside of the test vessel for heating the test solution; and
(c) a controller for controlling the heating element to control the temperature of the test solution, wherein the heating element comprises:
(1) a first heating area having a first power rating; and
(2) a second heating area having a second power rating different from the first power rating.

56. The apparatus of claim 55, wherein the test vessel comprises a reflective coating applied to a surface of the test vessel.

57. The apparatus of claim 55, wherein the stirring element comprises:
(1) a hollow shaft; and
(2) a temperature sensor located within the hollow shaft for generating signals representative of the temperature of the test solution when the hollow shaft is inserted into the test solution, wherein the controller controls the heating element in accordance with the signals from the temperature sensor.

58. The apparatus of claim 57, wherein the stirring element further comprises:
(3) a signal transfer device for transmitting the signals from the temperature sensor to the controller while the stirring element stirs the test solution.

59. The apparatus of claim 55, wherein the stirring element comprises:
  (1) a shaft adapted to be removably coupled to a plurality of different stirring element attachments.

60. The apparatus of claim 59, wherein the plurality of different stirring element attachments comprises a blade attachment and a basket attachment.

61. The apparatus of claim 55, further comprising:
  (d) a heater jacket surrounding the heating element for holding the heating element in place around the test vessel.

62. The apparatus of claim 61, wherein the heater jacket and heating element are configured to permit viewing of the stirring element through the front of the test vessel when the stirring element is inserted into the test vessel.

63. The apparatus of claim 61, wherein the heater jacket and heating element are configured to provide a gap between the outer surface of the heating element and the inner surface of the heater jacket.

* * * * *